(12) United States Patent
Delarge et al.

(10) Patent No.: US 6,818,765 B1
(45) Date of Patent: Nov. 16, 2004

(54) BENZENE-SULPHONAMIDE DERIVATIVES AND THEIR USES

(75) Inventors: Jacques Delarge, Sprimont (BE); Jean-Michel Dogne, Grivegnee (BE); Bernard Masereel, Fize-Fontaine (BE)

(73) Assignee: Universite de Liege, Liege (BE)

( * ) Notice: Subject to any disclaimer, the term of this patent is extended or adjusted under 35 U.S.C. 154(b) by 0 days.

(21) Appl. No.: 09/868,930

(22) PCT Filed: Jan. 12, 2000

(86) PCT No.: PCT/EP00/00225

§ 371 (c)(1),
(2), (4) Date: Oct. 16, 2001

(87) PCT Pub. No.: WO00/42004

PCT Pub. Date: Jul. 20, 2000

(30) Foreign Application Priority Data

Jan. 15, 1999 (EP) ................................................ 9900026

(51) Int. Cl.[7] ..................... C07D 223/04; C07D 295/10; C07D 307/02; C07C 67/02; C07C 275/00
(52) U.S. Cl. ............... 540/610; 514/217.12; 514/238.2; 514/471; 514/485; 514/508; 514/584; 514/592; 514/604; 544/160; 549/493; 558/8; 558/234; 560/12; 564/23; 564/42; 564/91
(58) Field of Search ..................... 514/217.12, 238.2, 514/471, 485, 508, 584, 592, 604; 540/610; 544/160; 549/493; 558/8, 234; 560/12; 564/23, 42, 91

(56) References Cited

U.S. PATENT DOCUMENTS 6,200,934 B1 * 3/2001 Muller et al. ................ 504/273
6,525,211 B1 * 2/2003 Muller et al. ................ 558/413

FOREIGN PATENT DOCUMENTS

DE     40 41 780 A1     6/1992
EP     0 044 807 A2     1/1982
EP     0 365 183 A1     4/1990

OTHER PUBLICATIONS

P. Wangemann et al., "CI –Channel Blockers in the Thick Ascending Limb of the Loop of Henle. Structure Activity Relationship", European Journal of Physiology, vol. 407, Suppl. 2, (1986), pp. S128–S141.

M. Wittner et al., "Analogues of Torasemide—Structure Function Relationships—Experiments in the Thick Ascending Limb of the Loop of Henle of Rabbit Nephron", European Journal of Physiology, vol. 408, No. 1, (1987), pp. 54–62.

Andrea Schlebe et al., "Acidity and Thermodynamical Metal Complex Stability Constants of Arylsulfonyl–Thioureas", Journal F. Prakt. Chemie, (1991), pp. 501–503.

XP–002114294, Nov. 1972, Abstract.

* cited by examiner

Primary Examiner—Brenda Coleman
(74) Attorney, Agent, or Firm—Jacobson Holman PLLC

(57) ABSTRACT

Benzene-sulphonamide derivatives complying with the general formula (I):

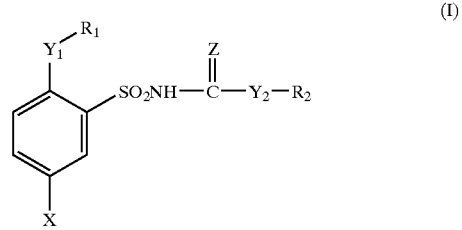

in which the different symbols have different meanings, their optical isomers and the salts pharmacologically acceptable of these derivatives, as well as their uses for drug manufacture and as radiolabelled pharmacological tools of the thromboxan A2 receptors.

6 Claims, No Drawings

BENZENE-SULPHONAMIDE DERIVATIVES AND THEIR USES

CROSS REFERENCES TO RELATED APPLICATIONS

This application is a national stage entry under 35 U.S.C. § 317 of PCT/EP00/00225, filed Jan. 12, 2000.

TECHNICAL DOMAIN

This invention relates to new benzene-sulphonamide derivatives and to their non-toxic salts as well as to their therapeutic uses.

DISCLOSURE OF THE INVENTION

The new benzene-sulphonamide derivatives, according to the invention, are represented by the general formula (I):

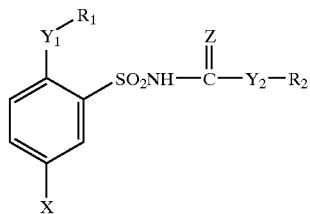

in which:

X represents a nitro, cyano, halogen group, eventually radioactive.

$Y_1$ represents a secondary or tertiary amino group, a sulphur or an oxygen;

$Y_2$ represents a nitrogen, an oxygen or a —NH group;

Z represents oxygen, sulphur, —N—CN or —CH—$NO_2$; and $R_1$ and $R_2$, which can be identical or different, represent each independently a linear or ramified alkyl group, saturated or unsaturated wit 2 to 12 carbon atoms, an alicyclic group, saturated or unsaturated with 3 to 12 carbon atoms, eventually radioactive, an aryl group, substituted or not by one or several alkyl groups in $C_1$–$C_4$, nitro, cyano, trifluoromethyl, carboxy and halogen, or an arylalkyl group, or $R_1$ and/or $R_2$ form with $Y_1$ and/or $Y_2$ a 5 to 7 membered heterocyclic group, saturated or unsaturated chains. with the exception of derivatives for which X is a nitro group,. $Y_1$ represents a secondary amine group (—NH—), $Y_2$ represents a —NH group, Z an oxygen, $R_2$ an isopropyl and $R_1$ an element selected in the group comprising (m-toluyl, phenyl and cyclooctyl) and with the exception of N-[(2-cyclooctylamino-5-cyanobenzene)sulfonyl]N'-isopropyl urea.

This invention refers also to optical isomers of benzene-sulphonamide derivatives covered by the formula (I) or to salts pharmacologically acceptable of these derivatives This invention refers also to salts of these derivatives, covered by the formula (I), by addition of non-toxic basis, for example to sodium and potassic salts, to salts with an organic acid, as an amino acid such as the lysine, the arginine, for example.

When, in the general formula (I), one has an asymmetrical carbon atom (as for example when $R_1$ and/or $R_2$ represent an arylalkyl group), the invention refers as well as to pure optical isomers than to the racemic mixture.

Preferred classes of compounds according to the formula (I) are, especially, those in which the X represents a nitro, cyano, bromo or iodo group, $Y_1$ represents a —NH group, $Y_2$ represents a —NH group or an oxygen atom and $R_1$ and $R_2$ represent each independently an ethyl, butyl, tert-butyl propyl, isopropyl, pentyl, hexyl, heptyl, octyl, decyl, amyl, cyclopropyl, cyclobutyl, cyclopentyl, cyclohexyl, cycloheptyl, cyclooctyl, cyclododecyl, 2-cyclohexenyl, m-toluyl, o-toluyl, p-toluyl, phenyl, allyl, adamantyl, norbornyl, caproyl, 3-carboxyphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,6-trimethylphenyl, furfuryl, benzyl or 1-phenylethyl group.

Another preferred class of these compounds is that in which $R_2$ and $Y_2$ form a homopiperidin group and that in which $R_1$ and $Y_1$ form a morpholin or homopiperidin group.

Still another particularly interesting class is that made by radioactive derivatives of the invention, and especially the derivatives in which X represents radioactive iodine, such that the $^{126}I$ and its radioactive isotopes $^{125}I$ and $^{131}I$, and those in which $R_1$ represents a saturated alicyclic group or unsaturated group with a tritium hydrogen in positions 2 and/or 3 of the cycle.

As one will see hereinafter in a more detailed way, the derivatives complying with the formula (I) are very useful in the prevention and/or treatment of illnesses involving the thromboxan $A_2$ at different levels, and especially in the cardiovascular and blood domains, pulmonary domain, reproduction domain and renal domain. They constitute also an excellent radiolabelled pharmacological tool of the thromboxan A2 receptors.

The present invention concerns, therefore, also the use of these benzene-sulphonamide derivatives and their salts for drug manufacture for the treatment and/or the prevention of the illnesses involving the thromboxan A2 as well as radiolabelled pharmacological tools of the thromboxan A2 receptors and of the pharmaceutical compositions containing these derivatives, these latter or their salts being used alone or in combination with excipients and/or other therapeutic agents having a similar or different activity.

The active compounds of the invention can be administered, according to the invention, under the form of a pharmaceutical composition, in association with different pharmaceutical excipients and this by oral, parenteral, rectal and topical way.

For the oral administration, one will use pills, granules, tablets, capsules, solutions, syrups, emulsions and suspensions containing classic excipients or additives in clinical pharmacy.

By parenteral way, the salts of active products could be administered in aqueous solution for example.

For the rectal administration, one will use suppositories and, by topical way, lotions, unguents, pomades, aerosols or nebulizers.

The active products can be used alone or in combination with other active products having a similar or different activity.

Among the compounds which give, in pharmaceutical use, very interesting results, we have to consider those in the formula (I), in which X represents a $NO_2$ or iodine group, $Y_1$ represents a secondary amino group, $Y_2$ represents a —NH group, Z represents an oxygen group, sulphur group or —N—CN group, and $R_1$ represents a cyclohexyl group, cycloheptyl group or cychlohexen-2-yl group, and $R_2$ an isopropyl group, tert-butyl group, pentyl group or homopiperidin group, and particularly considering the following compounds:

N-[(2-cyclohexylamin-5-nitrobenzene)sulfonyl]N'-tert-butyl urea,

N-cyano-N'-[(2-metatoluylamin-5-nitrobenzene)sulfonyl]homopiperidinoamidine,
N-[(2-cycloheptylamin-5-nitrobenzene)sulfonyl]N'-cyclohexyl thiourea, and
N-[(cyclohexen-2-yl)-5-iodobenzene)sulfonyl]N'-pentyl urea.

BEST WAY TO REALIZE THE INVENTION

Hereafter the definitions and explanations related to the synthesis of the derivatives of the invention are given.

The evolution of most reactions is followed by thin layer chromatography (T.L.C.). The plates are constituted of aluminium foils covered with silica gel 60F$_{254}$ (Merck®). The plate is examined by ultraviolet rays at 254 or 362 nm.

The elementary analysis (C, H, N, S) have been realized and correspond to the theoretic formula (+/−0,4%). The IR and [$^1$H]-RMN spectrums are in accordance with the proposed formulas.

The elementary analysis (C, H, N, S) have been determined on an Carlo Erba EA 1108 analizer.

The infrared spectrums of different substances (1 mg) have been registered by means of a FT-IR Perkin-Elmer 1750 under the form of KBr (250 mg) pellets.

After dissolution in the deuterium DMSO, the RMN-$^1$H spectrum of different molecules is registered on an Bruker 400 apparatus.

The melting points of the obtained molecules have been determined on an Buchi-Tottoli apparatus.

The general formula compounds (I) can be obtained easily by different way summarized in the hereafter synthetic schemes.

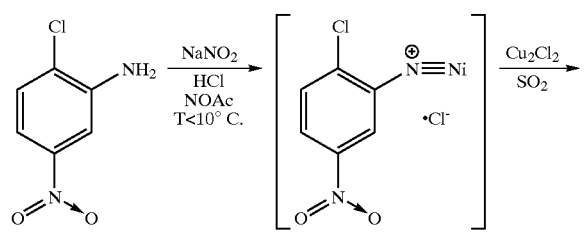

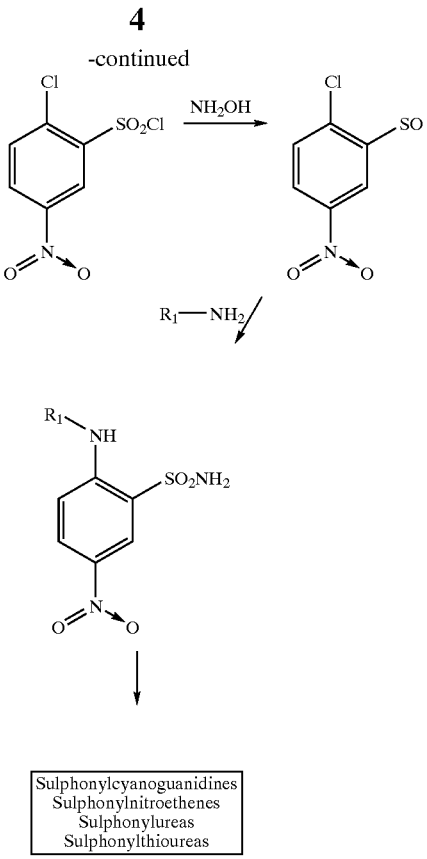

The 2-chloro-5-nitroaniline is diazotised at a temperature comprised between 0 and 10° C. The diazonium salt formed is substituted in presence of copper salts (catalyst) by sulphur anhydride to generate sulphochloride which in presence of ammonia forms the corresponding 2-chloro-5-nitrobenzenesulfonamide. The chlorine is then substituted by an adequate amine.

The adequated sulphonylurea, thioureas, cyanoguanidines and nitroethenes functions are obtained by condensation of selected reactives (isocyanates for sulphonylureas or isothiocyanates for sulfonylthioureas) or prepared (N-cyano-N'-alkyl (or aryl)carbamimidothioate of S-methyl for sulfonylcyanoguanidines and 1-alkyl (or aryl)amino-1'-methylthio-2-nitroethylene for sulfonitroethenes) on the sulphonamide sodium salt obtained by reaction with exactly 1 sodium hydroxyde equivalent.

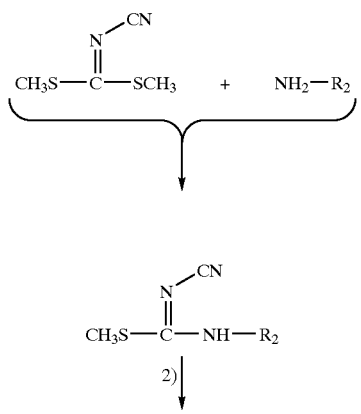

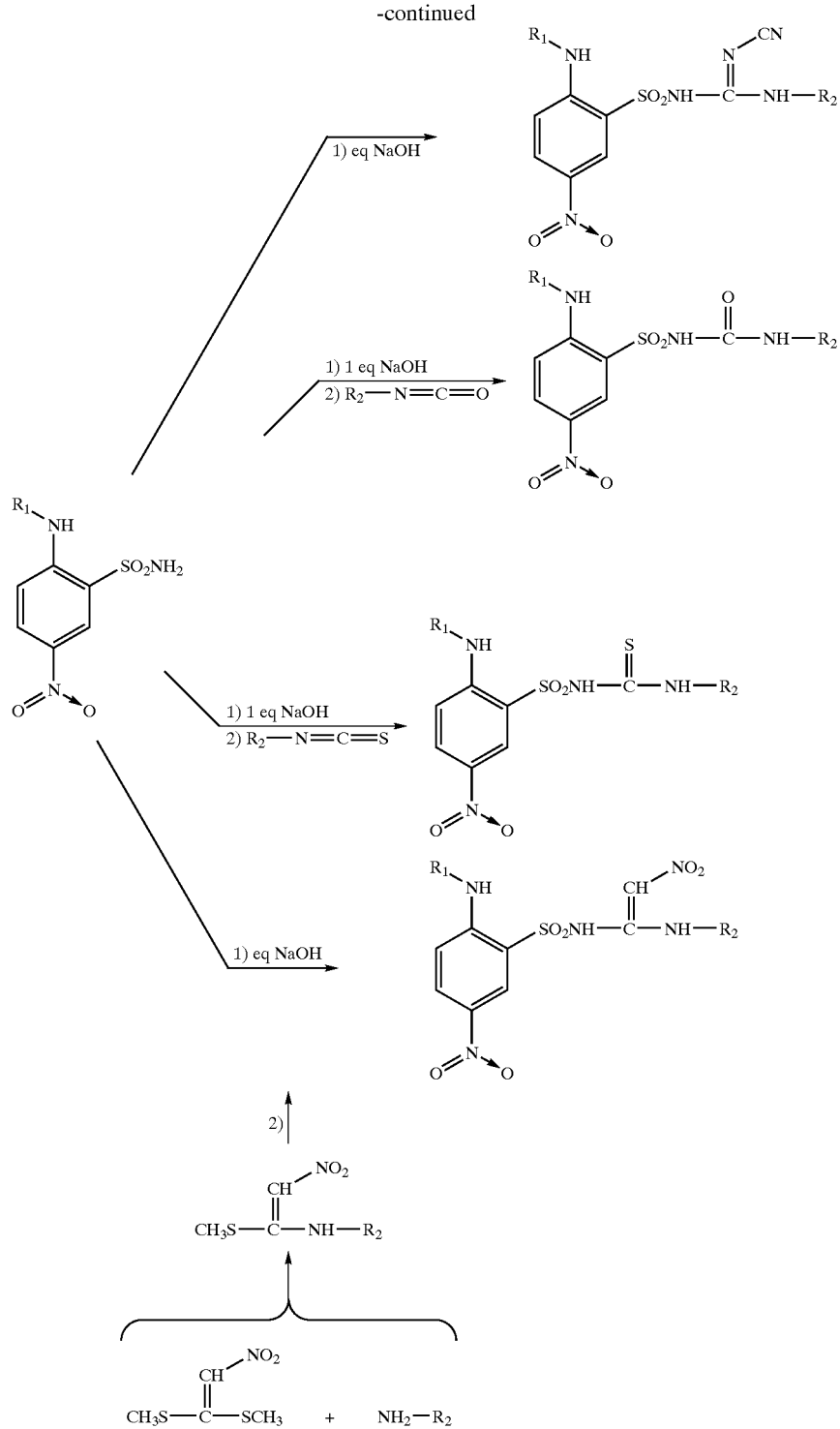

1.1.) 2-Chloro-5-nitrobenzenesulfonamide

On the one hand, one saturates 160 ml of anhydrous acetic acid in $SO_2$ for 5 hours (solution A), on the other hand, 10 g of 2-chloro-5-nitroaniline are dissolved in 40 ml of 12 N hydrochloric acid and 100 ml of anhydrous acetic acid (solution B). This solution is cooled till reach a temperature near 0 to −5° C. Finally, one dissolves 7 g of sodium nitrite in 10 ml of water (solution C). The solution C is added drop by drop to solution B to form the diazonium salt. The temperature must be maintained towards −5° C. 4 g of $CuCl_2$ are dissolved in 10 ml of water (solution D). The solution D is added to solution A and agitated for 2 minutes. A precipitate of $Cu_2Cl_2$ appears. The diazonium solution is then prudently and under agitation added to this suspension then 180 g of ice is added in the reaction medium. The precipitate of sulphonyl chloride is rapidly collected on filter, washed with cold water and added under agitation to a previously cooled solution, realized with 50 ml of concentrated ammonia and 100 ml of water. After filtration and clarification with charcoal, the filtrate is concentrated under reduced pressure. The pH is adjusted to 5–6 by 10 N hydrochloric acid. After cooling, the sulphonamide is collected on filter, washed with water and dried. Then it is eventually recrystallized with methanol.

| Yield: | 50–60%. |
|---|---|
| Melting point: | 178° C. |
| Molecular Weight: | 236.62 ($C_6H_5ClN_2O_4S$) |

1.2.) 2-Alkyl (or acyl)amino-5-nitrobenzenesulfonamides 10 g of 2-chloro-5-nitrobenzenesulfonamide prepared in 1.1.) are put in solution in 50 ml of 3-chlorotoluene with 15 ml of amine. One heats about 3 hours, under nitrogen. The reaction is followed by thin layer chromatography. At the term, the solution is filtered, then concentrated under reduced pressure. The residue is retaken by a sodium hydroxyde solution at 2% and purified with charcoal. One brings to pH 1 by 2N hydrochloric acid. The suspension is extracted three times by 100 ml of diethylic ether. The ether is evaporated under reduced pressure. The residue is retaken by a sodium hydroxyde solution at 2%, then clarified with charcoal and brought to pH 7.5-8 by 5N hydrochloric acid.

The precipitate of 2-alkyl (or aryl)amino-5-nitrobenzenesulfonamide is collected on filter, washed and recrystallized with methanol.

1.3.) Sulphonylureas
N-[(2-alkyl (or aryl)amino-5-nitrobenzene)sulfonyl] N'-alkyl (or aryl) ureas One dissolves 0.01 mole of suitable sulphonamide prepared in 1.2.) in 30 ml of a water-acetone mixture (50/50 vol/vol). After having added a sodium hydroxyde equivalent (solution at 10%), one adds 0.02 mole of adequate isocyanate. For weak volatile isocyanates (B.P. >90° C.), the solution is brought to reflux under agitation while for volatile isocyanates (isopropyl-, ethyl-, methylisocyanate), the solution is placed under agitation at room temperature. The progression of the reaction is followed by thin layer chromatography. At the end, the reaction medium is evaporated under depression, the residue is retaken by 100 ml of sodium hydroxyde at 2%. This solution is extracted three times by 150 ml of diethylic ether then clarified with charcoal. The aqueous phase is brought to pH 7.5 by 2N hydrochloric acid. The sulphonylurea which precipitates is collected on filter, washed with water and dried. The product is eventually recrystallized in diluted alcohol.

Examples of compounds prepared according to this process (Table 1): n° 1; 2; 13; 17; 19; 20; 21; 22; 23; 25; 26; 27; 28; 29; 30; 31; 32; 33; 34; 44; 46; 47; 48; 49; 50; 52; 53; 54; 55; 56; 57; 58; 59; 60; 61; 62; 63; 64; 65; 67; 73; 75; 76; 77; 78; 79; 80; 81; 82; 83; 84; 85; 86; 87; 88; 89; 90; 91; 92; 94; 95; 96.

1.4.) Sulfonylthioureas
N-[(2-alkyl (or aryl)amino-5-nitrobenzene)sulfonyl] N'-alkyl (or aryl) thioureas 0.01 mole of suitable sulphonamide prepared in 1.2.) is dissolved in 30 ml of a water-acetone mixture (50/50 vol/vol). After having added a sodium hydroxyde equivalent (solution at 10%), 0.02 mole of adequate isothiocyanate is added. For weak volatile isothiocyanates (B.P. >90° C.), the solution is brought to reflux under agitation while for volatile isothiocyanates (isopropyl, ethyl, methylisothiocyanate), the solution is placed under agitation at room temperature. The progression of the reaction is followed by thin layer chromatography. At the end, the reaction medium is evaporated under depression, the residue is retaken by 100 ml of sodium hydroxyde at 2%. This solution is extracted three times by 150 ml of diethylic ether then clarified with charcoal. The aqueous phase is brought to pH 7.5 by 2N hydrochloric acid. The sulfonylthiourea which precipitates is collected on filter, washed with water and dried. The product is eventually recrystallized in diluted alcohol.

Examples of compounds prepared according to this process (Table 1): n° 11; 12; 14; 15; 16; 35; 36; 37; 38; 39; 40; 41; 50.

1.5.) Sulfonylcyanoguanidines
1.5.1.) N-cyano-N'-alkyl (or aryl)carbamimidothioates of S-methyl One allows to react 0.05 mole of dimethyl N-cyanodithioiminocarbonate with 0.075 mole of adequate amine in 10 ml of ethanol. This solution is heated under reflux for 15 to 20 hours (for volatile amine, the reaction itself will proceed at room temperature). The progression of the reaction is followed by thin layer chromatography. At the end, the solution is cooled under ice cold water and the precipitate collected on filter, then it is recrystallized into boiling methanol.

1.5.2.) N-[(2-alkyl (or aryl)amino-5-nitrobenzene)sulfonyl] N'-alkyl cyanoguanidines 0.01 mole of suitable sulphonamide prepared in 1.2.) is dissolved in 5 ml of a water-acetone mixture (50/50 vol/vol) and then 0.01 mole of sodium hydroxyde is added (solution at 10%). This solution is placed under agitation for 10 minutes then concentrated under reduced pressure. The residue (sulfonamidate) is solubilized in a mixture constituted of 3 ml of dioxane and 2 ml of dimethylformamide then added with 0.015 mole of adequate S-methyl-N-cyano-N'-alkylcarbamimidothioate prepared in 1.5.1.). This solution is brought to reflux under agitation. The progression of the reaction is followed by thin layer chromatography. At the end of the reaction, the solution is concentrated under reduced pressure then added with 100 ml of sodium hydroxyde at 2%. This solution is extracted three times by 150 ml of diethylic ether then clarified with charcoal. The aqueous phase is brought to pH 7.5 by hydrochloric acid 2N. The precipitate is collected on filter, washed with water and dried. The product is eventually recrystallized into methanol.

T.L.C.:ethyl acetate 13/cyclohexane 7.

Examples of compounds prepared according to this process (Table 1): n° s 3; 4; 5; 6; 7; 8; 9; 18; 51; 74.

1.6.) Sulfonylnitroethenes
1.6.1.) 1-Alkyl (or aryl)amino-1'-methylthio-2-nitroethylnes One allows to react 0.05 mole of 1,1'-bis(methylthio)-2-nitroethylene with 0.075 mole of adequate amine in 10 ml of ethanol. This solution is brought under reflux 15 to 20 hours (for volatile amine, the reaction itself will proceed to room temperature). The progression of the reaction is followed by thin layer chromatography. At the end, the solution is cooled under ice cold water and added with 30 ml of water. The obtained precipitate is collected on filter, then recrystallized with boiling methanol. T.L.C.:ethyl acetate 8/petroleum ether PE 40/60 12.

1.6.2.) 1-Alkyl (or aryl)amino-1'-[2-alkyl (or aryl)amino-5'-nitrobenzenesulfonamide]-2-nitroethylnes 0.01 mole of suitable sulphonamide prepared in 1.2.) is dissolved in 5 ml of a water-acetone mixture (50/50 vol/vol), then 0.01 mole of sodium hydroxyde is added (solution at 10%). This solution is placed under agitation for 10 minutes then concentrated under reduced pressure. The residue (sulfonamidate) is solubilized in a mixture constituted of 3 ml of dioxane and 2 ml of dimethylformamide then added with 0.015 mole of 1-alkyl (or aryl)amino-1'-methylthio-2-nitroethylne adequately prepared in 1.6.1). This solution is brought to reflux under agitation. The progression of the reaction is followed by thin layer chromatography. At the end of the reaction, the solution is concentrated under reduced pressure then added with 100 ml of sodium hydroxyde at 2%. This solution is extracted three times with 150 ml of diethylic ether then clarified with charcoal. The aqueous phase is brought to pH 7.5 by 2N hydrochloric acid. The precipitate is collected on filter, washed with water and dried. The product is eventually recrystallized into methanol.

T.L.C.:ethyl acetate 8/petroleum ether PE 40/60 12.

Composition example prepared following this process (Table 1): n' 10.

1.7.) Sulfonylcarbamates

2-Alkyl (or aryl)amino-5-nitrobenzenesulfonylcarbamates of ethyl 0.01 mole of sulphonamide prepared in 1.2.) is dissolved in 10 ml of anhydrous pyridine. Under agitation, drop by drop, a large excess (10 ml) of ethyl chloroformiate is added. The evolution of the synthesis is followed by thin layer chromatography. At the end of the reaction, about 15 minutes after having added the chloroformiate, the solution is evaporated under reduced pressure and the residue retaken by 100 ml of sodium hydroxyde at 2%. After two extractions by 150 ml of diethylic ether, the alkaline solution is clarified with charcoal then neutralized to pH 6.5 with 2N hydrochloric acid. The carbamate precipitate is collected, washed with water and dried under vacuum.

Yield: 75%–88%

T.L.C.:ethyl acetate, methanol and triethylamine 18/211.

Example of compounds prepared according to this process (Table 1): n° 45.

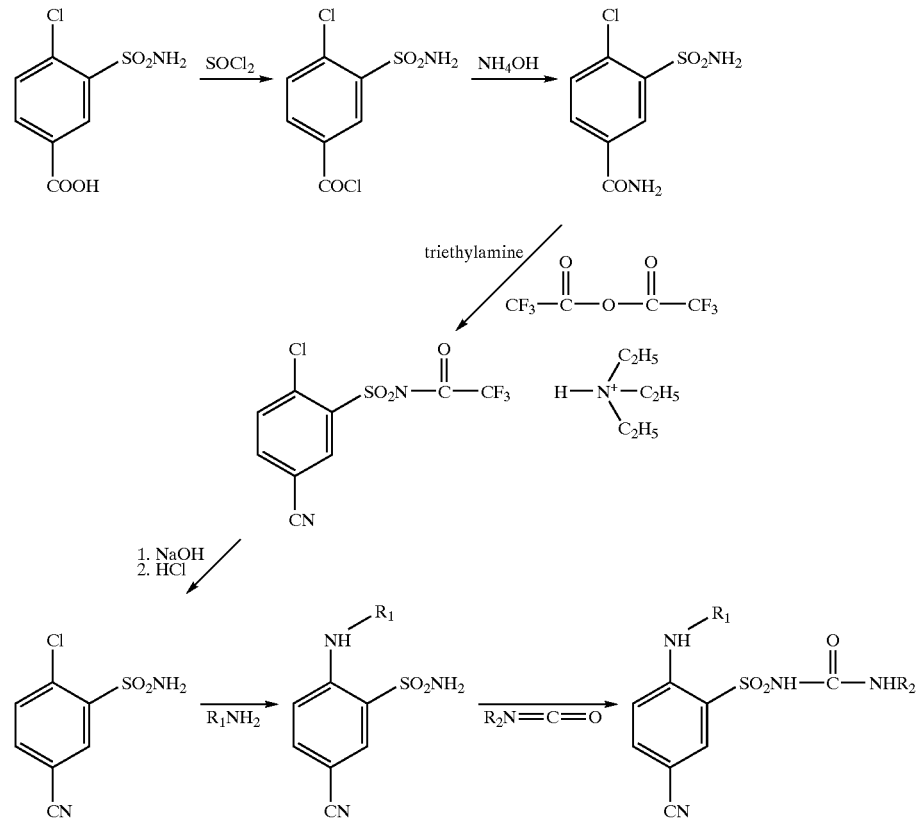

Scheme 2 Derivatives of benzonitrile

The 4-chloro-3-sulfamoylbenzoic acid is put in reaction with the thionyl chloride to form the acid chloride which, in presence of ammonia, generates the corresponding carboxamide. The latter is dehydrated in presence of trifluoroacetic anhydride. The acylsulphonamide at the moment of this reaction is hydrolyzed in presence of exactly 2,5 sodium hydroxyde equivalent. The sulphonamide is then regenerated to pH acid. The chlorine is then substituted by an adequate amine. The sulphonylurea function is obtained by condensation of the isocyanate chosen on the previously sulphonamide sodium salt prepared by reaction with exactly 1 sodium hydroxyde equivalent. The carboxylic function is then regenerated by alkaline hydrolysis of the benzonitrile.

2.1.) 4-Chloro-3-sulfamoylbenzenecarboxamide

One allows to react 0.01 mole of acid 4-chloro-3-sulfamoylbenzoic with 25 ml of thionyl chloride. This solution is brought to reflux for 3 hours. At the end, the reaction medium is concentrated under reduced pressure, then added with 10 ml of dioxane. This solution is added under agitation at a previously cooled solution realized with 25 ml of concentrated ammonia and with 50 ml of water. The excess of ammonia is eliminated under reduced pressure. The precipitate is collected on filter, washed with water and dried. It is eventually recrystallized into methanol.

| | |
|---|---|
| Yield: | 50–60% |
| Point of fusion: | 220–222° C. |
| Molecular weight: | 234.656 ($C_7H_7ClN_2O_3S$). |
| T.L.C.: | ethyl acetate 18/methanol 4/formic acid 5 drops. |

2.2.) 4-Chloro-3-sulfamoylbenzonitrile

To 0.01 mole of 4-chloro-3-sulfamoylbenzenecarboxamide 80 ml of anhydrous tetrahydrofurane are added. This suspension is cooled at 0° C. then successively added with 0.045 mole of triethylamine and 0.02 mole of trifluoracetic anhydride. The progression of the reaction is followed by thin layer chromatography. At the end, the reaction medium is concentrated under depression. The residue is retaken by water, filtered and washed. The obtained product is put in reaction with 2.5 equivalent of 2N sodium hydroxyde solution for a maximum of 30 minutes. The solution is then brought to pH 1 by 2N hydrochloric acid. The precipitate is then rapidly collected on filter, washed with water and dried.

| | |
|---|---|
| Yield: | 70–80% |
| Melting point: | 199–201° C. |
| Molecular weight: | 216.64 ($C_7H_5ClN_2O_2S$). |
| Elementary analysis: found: | +/−0.4% of calculated. |
| T.L.C.: | ethyl acetate 18/methanol 4/formic acid 5 drops. |

2.3.) 4-Alkyl (or aryl)amino-3-sulfamoylbenzonitriles

One processes as in 1.2.) by using the 4-chloro-3-sulfamoylbenzonitrile as raw material.

2.4.) N-[(2-alkyl (or aryl)amino-5-cyanobenzene)sulfonyl] N'-alkyl (or aryl) ureas One processes as in 1.3.) by using 4-alkyl (or aryl)amino-3-sulfamoylbenzonitrile as raw material.

Examples of compounds prepared according to this process (Table 1): n° 24; 43; 66; 97.

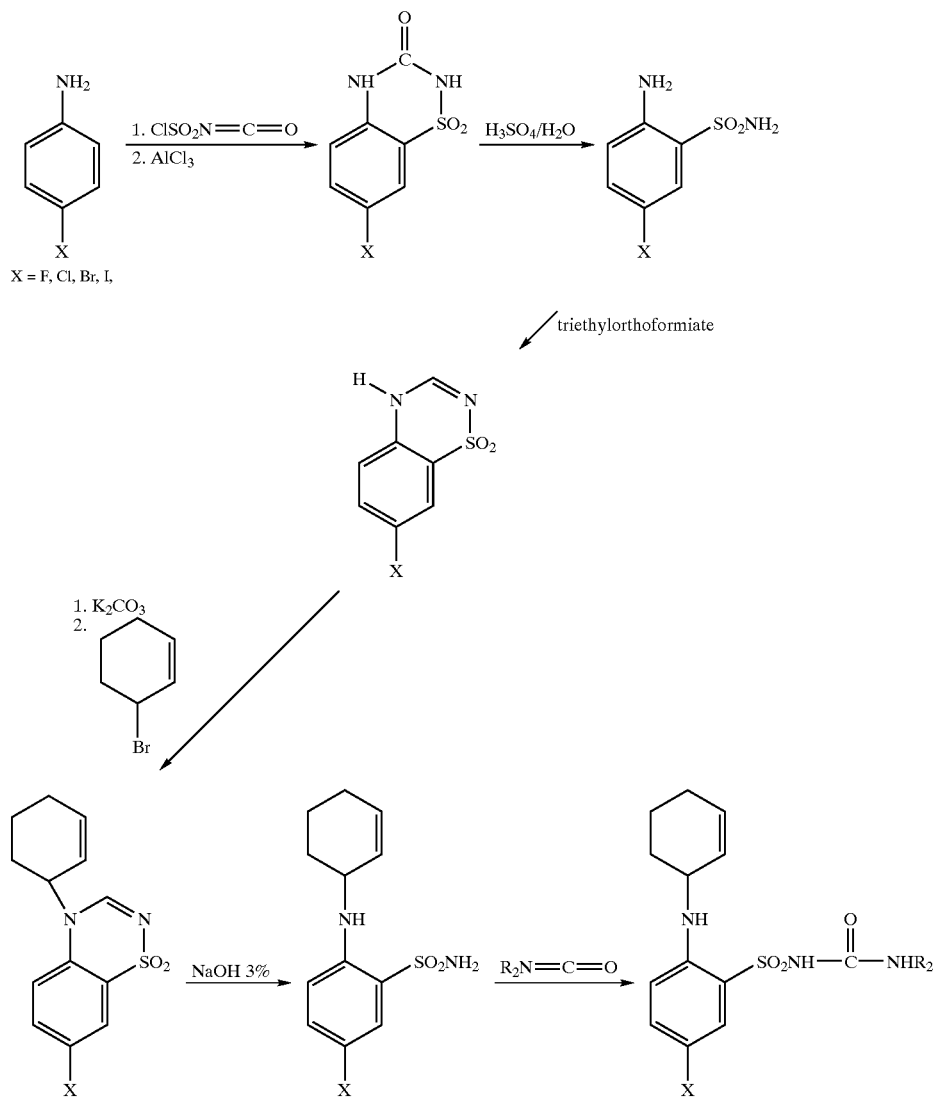

Scheme 3 Halogenobenzenic derivatives

Halogenobenzenic derivatives

The adequate aniline is placed in reaction with a light excess of chlorosulfonylisocyanate at a temperature of −5° C. Aluminium chloride is then added in the medium in order to obtain the following cyclic product: 2,3-dihydro-7-halogeno-3-oxo4H-1,2,4-benzothiazidine 1,1-dioxyde. The latter is hydrolyzed by treatment in sulphuric medium. The aminosulfonamide is then engaged in a new reaction of cyclization to the triethyl orthoformiate. The 7-halogeno-4H-1,2,4-benzothiadiazine 1,1-dioxide obtained is alkyled in position 4 with the 3-bromocyclohexene in presence of 4 potassic carbonate equivalent. The 2-(cyclohexene-2-yl) amino-5-halogenobenzenesulfonamide is then generated by sodium hydroxyde treatment. The sulphonylurea function is obtained by condensation of the chosen isocyanate on the previously sulphonamide sodium salt prepared by reaction with exactly 1 sodium hydroxyde equivalent.

3.1.) 2.3-Dihydro-7-halogeno-3-oxo-4H-1.2.4-benzothiadiazine 1.1-dioxydes 0.07 mole of chlorosulfonylisocyanate is solubilised in 90 ml of nitromethane previously cooled at −5° C., then drop by drop, 50 ml of a solution of nitromethane containing 0.06 mole of adequate amine, is added. One add drop by drop 0.097 mole of aluminium chloride in the medium. The solution is heated under reflux for 45 minutes, then poured on ice. The obtained precipitate is collected on filter, washed with water and dried. The product is eventually purified by redissolution in a sodium bicarbonate aqueous solution (5% m/vol) and reprecipitation by 2N hydrochloric acid addition.

Yield: 70–75%

T.L.C.: ethyl acetate 20/formic acid 5 drops.

3.2.) 2-Amino-5-halogenobenzenesulfonamides 0.01 mole of 2,3-dihydro-7-halogeno-3-oxo-4H-1,2,4-benzothiadiazine 1,1-dioxyde prepared in 5.1.) is added to 100 ml of a sulphuric-acid water mixture (50/50). The reaction medium is carried to reflux for one hour. After cooling, the solution is brought to pH 3 by sodium hydrozyde at 30%. The obtained precipitate is collected on filter, washed with water and dried.

| Yield: | 80–85% |
|---|---|
| T.L.C.: | ethyl acetate 13/cyclohexane 7/formic acid 5 drops. |

3.3.) 7-Halogeno-4H-1.2.4-benzothiadiazine 1.1-dioxides 0.01 mole of 2-amino-5-halogenobenzenesulfonamide prepared in 5.2.) is dissolved in 25 ml of triethylorthoformiate. The reaction medium is carried to reflux for one hour. After cooling, the precipitate is collected on filter, washed and dried.

| Yield: | 50–60% |
|---|---|
| T.L.C.: | ethyl acetate 13/cyclohexane 7/formic acid 5 drops. |

3.4.) 4-(Cyclohexen-2-yl)7-halogeno-1,2,4-benzothiadiazine 1,1-dioxydes

One puts in suspension 0.01 mole of 7-halogen-4H-1,2,4-benzothiadiazine 1,1-dioxide prepared in 5.3.) in 300 ml of acetonitrile containing 0.04 mole of potassic carbonate. The reaction medium is carried to reflux 30 minutes then added with 0.04 mole of 3-bromocyclohexene. The reflux is maintained during 4 hours. The reaction is followed by thin layer chromatography. At the end, the potassic carbonate in excess is collected on filter. The filtrate is concentrated under reduced pressure. The residue is added with 50 ml of methanol carried to ebullition. The precipitate is collected on filter, washed and dried.

| Yield: | 60–70% |
|---|---|
| T.L.C.: | ethyl acetate 13/cyclohexane 7/formic acid 5 drops. |

3.5.) 2-(Cyclohexen-2-yl)amino-5-halogenobenzene-sulphonamides

To 0.01 mole of 4-(cyclohexen-2-yl)-7-halogeno-1,2,4-benzothiadiazine 1,1-dioxide prepared in 5.4) is added 50 ml of sodium hydroxyde at 3%. The suspension is brought to 60° C. for twelve hours. At the end, the solution is brought to pH 7 by 5 N hydrochloric acid. The obtained precipitate is collected on filter, washed with water and dried.

| Yield: | 50–60% |
|---|---|
| T.L.C.: | ethyl acetate 13/cyclohexane 7/formic acid 5 drops. |

3.6.) N-[(2-cyclohexen-2-yl)-5-halogenobenzene)sulfonyl] N'-alkyl (or aryl)urea

One processes as in 1.3.) by using 2-(cyclohexen-2-yl) amino-5-halogenobenzenesulfonamide as raw material. Examples of compounds prepared according to this method (Table 1): n° 68; 69; 70; 71; 72.

The Table 1 given hereinafter refers to preparation of a composed series complying with the general formula (I).

As already specified, the new benzene-sulphonamide derivatives so described are interesting in prevention and/or the treatment of the illnesses involving thromboxan $A_2$ at different levels and especially:

Cardio-vascular and blood diseases:
    Myocardial infarction,
    Thrombus formation and vascular lesions,
    Haemostasis diseases,
    Atherosclerosis,
    Arteriosclerosis,
    Myocardial ischemia,
    Arterial hypertension.
Pulmonary:
    Asthma,
    Bronchospasm,
    Pulmonary hypertension.
Of the reproduction:
    Preeclampsia.
Renal:
    Renal hypertension,
    Renal dysfunction.

The derivatives of the invention are also interesting for the conception of an original radiolabelled pharmacological tool of thromboxan A2 receptors. The following scheme 6 shows this kind of application from the compounds n° 80 and 104 (Table 1).

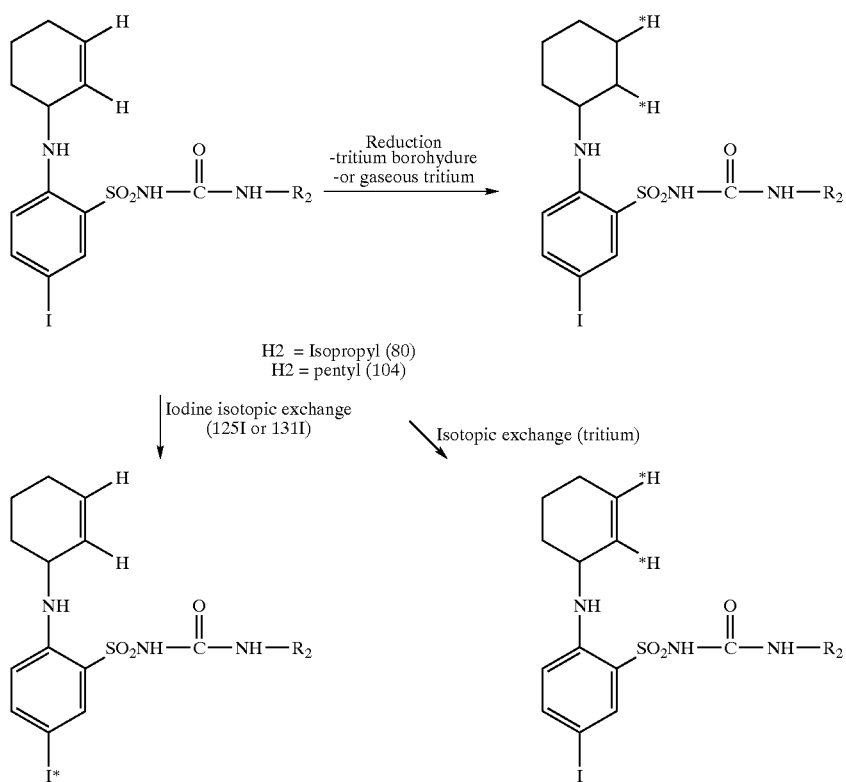

H2 = Isopropyl (80)
H2 = pentyl (104)

As we can see, two labelling technics are considered:
A tritium marking technique ($^3$H).
either by reduction with a tritium reducer:(tritium hydrogen or tritium borohydrure).
either by isotope exchange.
An iodine labelling technic ($^{125}$I or $^{131}$I) by isotope exchange.

What follows and the tables hereinafter refer to results of pharmacological tests realised on a certain number of compounds given into Table 1.

To operate a first selection, the capacity of these compounds to displace in a specific way a tritium ligand, the [$^3$H] SQ-29.548, from the thomboxan $A_2$ receptor of human platelets have been examined. This binding test is, in fact, simple, fast and allows so a selection of products which have a strong affinity for thromboxan A2 platelet receptors (TPα).

The $TXA_2$ antagonist potency of the selected compounds has been evaluated by a platelet aggregation test induced by the U-46619 (stable agonist of the thromboxan A2) or by the arachidonic acid.

Two tests on smooth musculature have allowed to confirm the antagonist potency on the TPτ thromboxan A2 receptors. Indeed, the capacity of the selected compounds during the binding to prevent the contraction of the rat fundus induced by l'U-46619 and to relax the rat aorta precontracted by this same stable agonist of the $TXA_2$ have been evaluated;

All the results are recorded in parallel with those of two thromboxan A2 receptors antagonists described in literature and which are the object of in-depth clinical studies: the sulotroban and the SQ-29.548.

The SQ-29.548 and the U46619 are respectively the acid [1S-[1-alpha,2-beta (5Z),3-beta, 4-alpha]-7-[3-[[2-(phenylamino)carbonyl]hydrazin]methyl]-7-oxabicyclo [2.2.1]hept-2-yl]-5-heptenoic and the 9,11-didesoxy, 11-alpha, 9-alpha-epoxy-methanoprostaglandine $F_{2a}$.

The materials and methods used for pharmacological tests are those described in literature.

TABLE 2

Binding to human platelets thromboxane $A_2$ receptors
Binding Test Results on human platelets

| COMPOUND NUMBER | BINDING TEST | | |
|---|---|---|---|
| | $10^{-6}$M: (%)[1] AFFINITY | $10^{-7}$M: (%)[1] AFFINITY | IC 50[2] (ηM) |
| SULOTROBAN | 55.6 | 16.5 | 1100 |
| SQ-29.548 | 100 | 72.0 | 23.2 |
| 1 | 93.6 | 68.0 | |
| 2 | 67.7 | | |
| 3 | 20.1 | | |
| 4 | 50.0 | | |
| 5 | 72.1 | | |
| 6 | 29.8 | | |
| 7 | 42.9 | | |
| 8 | 33.0 | | |
| 9 | 15.4 | | |
| 10 | 57.7 | | |
| 11 | 63.7 | | |
| 12 | 67.2 | | |
| 13 | 97.7 | 60.3 | |
| 14 | 92.9 | 34.0 | |
| 15 | 81.0 | 16.6 | |
| 16 | 100 | 46.1 | |
| 17 | 100 | 88.0 | 22.7 |
| 18 | 100 | 88.9 | 24.2 |
| 19 | 97.8 | 93.3 | 3.96 |
| 20 | 1.6 | | |
| 21 | 92.2 | 44.2 | |
| 22 | 100 | 84.1 | 41.7 |
| 23 | 95.5 | 62.9 | |
| 24 | 73.7 | | |
| 25 | 100 | 95.2 | 10.5 |

TABLE 2-continued

Binding to human platelets thromboxane $A_2$ receptors
Binding Test Results on human platelets

| COMPOUND NUMBER | BINDING TEST | | |
|---|---|---|---|
| | $10^{-6}$M: (%)[1] AFFINITY | $10^{-7}$M: (%)[1] AFFINITY | IC 50[2] ($\eta$M) |
| 26 | 94.3 | 93.3 | 16.9 |
| 27 | 79.6 | | |
| 28 | 81.9 | 39.6 | |
| 29 | 97.4 | 95.4 | 7.8 |
| 30 | 95.1 | 80.8 | |
| 31 | 80.5 | 42.2 | |
| 32 | 86.7 | 46.0 | |
| 33 | 86.6 | 52.4 | |
| 34 | 77.3 | | |
| 35 | 45.0 | | |
| 36 | 75.6 | | |
| 37 | 72.3 | | |
| 38 | 77.2 | | |
| 39 | 74.5 | | |
| 40 | 94.4 | 63.0 | 26.9 |
| 41 | 75.9 | | |
| 42 | 92.3 | 50.5 | |
| 43 | 50.0 | | |
| 44 | 80.2 | 51.3 | |
| 45 | 79.9 | 50.4 | |
| 46 | 1.4 | | |
| 47 | 98.7 | 89.4 | |
| 48 | 51.9 | | |
| 49 | 98.3 | 94.9 | 2.0 |
| 50 | 95.7 | 76.0 | |
| 51 | 64.7 | | |
| 52 | 99.0 | 93.9 | 2.8 |
| 53 | 36.5 | | |
| 54 | 91.7 | | |
| 55 | 98.2 | 93.3 | 3.4 |
| 56 | 0.0 | | |
| 57 | 67.0 | | |
| 58 | 83.2 | | |
| 59 | 92.2 | | |
| 60 | 79.1 | | |
| 61 | 98.6 | 94.8 | 1.1 |
| 62 | 3.7 | | |
| 63 | 7.5 | | |
| 64 | 57.8 | | |
| 65 | 46.6 | | |
| 66 | 49.6 | | |
| 67 | 98.3 | 95.8 | 1.3 |
| 68 | 93.2 | 67.4 | |
| 69 | 13.2 | | |
| 70 | 63.8 | | |
| 71 | 77.8 | | |
| 72 | 86.5 | 52.7 | |
| 73 | 98.3 | 95.6 | 1.2 |
| 74 | 90.9 | | |
| 75 | 93.1 | | |
| 76 | 97.6 | 93.5 | 3.5 |
| 77 | 79.4 | | |
| 78 | 95.3 | 71.6 | 4.2 |
| 79 | 96.6 | | |
| 80 | 98.6 | 97.9 | 2.4 |
| 81 | 93.3 | 65.0 | 57.8 |
| 82 | 98.5 | 98.0 | 4.5 |
| 83 | 98.5 | 92.7 | 4.5 |
| 84 | 96.9 | 73.7 | 23.9 |
| 85 | 92.9 | 42.5 | 107.2 |
| 86 | 98.4 | 94.3 | 1.83 |
| 87 | 95.6 | 76.0 | 18.1 |
| 88 | 95.4 | 82.0 | 16.2 |
| 89 | 96.6 | 83.5 | 11.5 |
| 90 | 96.9 | 88.6 | 5.46 |
| 91 | 97.3 | 90.8 | 3.31 |
| 92 | 98.8 | 95.2 | 1.62 |
| 93 | 97.9 | 90.2 | 7.8 |
| 94 | 98.4 | | 2.82 |

TABLE 2-continued

Binding to human platelets thromboxane $A_2$ receptors
Binding Test Results on human platelets

| COMPOUND NUMBER | BINDING TEST | | |
|---|---|---|---|
| | $10^{-6}$M: (%)[1] AFFINITY | $10^{-7}$M: (%)[1] AFFINITY | IC 50[2] ($\eta$M) |
| 95 | 98.5 | | 1.45 |
| 96 | 92.3 | | 43.95 |
| 97 | 89.7 | | 98.48 |
| DEVIATION STANDARD <5% | | | |

[1]Affinity means the percent of [$^3$H]SQ-29.548 specifically substituted by the examined compound.
[2]IC 50: Means the concentrations required for replacing 50% of [$^3$H]SQ-29.548 bound to receptors TPα.

1 Affinity means the per cent of [$^3$H]SQ-29.548 specifically substituted by the examined compound.

2 IC 50:Means the concentrations required for replacing 50% of [$^3$H]SQ-29.548 bound to receptors TPα.

Test according to:

Cozzi P., Giordani A., Menichincheri M., Pillan A., Pinciroli V., Rossi A., Tonani R., Volpi D., Tamburin M., Ferrario R., Fusar D., Salvati P.,—Agents combining thromboxane receptor antagonism with thromboxane synthase inhibition:[[[2-(1H-imidazol-1-yl)ethylidene]amino]oxy]alkanoic acids.—*J. Med. Chem.,* 1994, 37, 3588–3604.

TABLE 3

Platelet Aggregation
Test Results on Human Platelets aggregation

| | AGGREGATION PLATELET TEST | |
|---|---|---|
| COMPOUND | ARACHIDONIC ACID IC 50[1] ($\mu$M) | U-46.619 IC 50[1] ($\mu$M) |
| SULOTROBAN | 11.7 | 10.5 |
| SQ-29.548 | 0.035 | 0.034 |
| 18 | 0.36 | 0.48 |
| STANDARD DEVIATION <5% | | |

[1]IC 50: Means concentrations required for reduction by 50% the platelet aggregation induced by 0.6 nM of arachidonic acid (AA) or by 30 nM of U-46619.

Test described according to:

Born G.V.R., Cross M. J.,—The aggregation of blood platelets.—*J. Physiol.,* 1963, 168, 178–195.

Tsuyoshi T., Masayuki Y., Shuichi W., Kazuhiro K., Takashi Y.,—Designe, synthesis, and pharmacology of 3-substituted sodium azulene—1 sulfonates and related compounds: Non-prostaboid thromboxane $A_2$ receptor antagonists.—*J. Med. Chem.,* 1993, 36, 791–800.

TABLE 4

Rat Aorta Contraction
Test results of Rat Aorta Contraction

| COMPOUND | AORTA RAT CONTRACTION TEST IC 50[1] ($\eta$M) |
|---|---|
| SULOTROBAN | $1.6 \cdot 10^3$ |
| SQ-29.548 | 31.8 |
| 17 | 1.38 |
| 18 | 1.21 |
| 22 | 37.6 |

TABLE 4-continued

Rat Aorta Contraction
Test results of Rat Aorta Contraction

| COMPOUND | AORTA RAT CONTRACTION TEST IC 50[1] (ηM) |
|---|---|
| 25 | 19.7 |
| 29 | 20.6 |
| 40 | 17.7 |
| STANDARD DEVIATION <5% | |

[1]IC 50: Means the compounds concentrations reducing by 50% the Rat Aorta muscular tonus induced by U-46619 (0.03 μM).

Test desribed according to:
de Tullio P., Pirotte B., Lebrun P., Fontaine J., Dupont L., Antoine M. H., Ouedraogo R., Khelili S., Maggetto C., Masereel B., Diouf O., Podona T., Delarge J., 3-and -4-substituted 4H-pyrido[4,3-e]-1,2,4-thiadiazine 1,1-dioxides as potassium channels openers: synthesis pharmacological evaluation, and structure-activity relationships.— *J. Med. Chem.*, 1996, 39, 937–948.

TABLE 5

Rat Fundus Contraction
Test Results for preventing contraction of rat fundus

| COMPOUND | TEST FOR PREVENTING THE RAT FUNDUS CONTRACTION IC 50[1] (μM) |
|---|---|
| SULOTROBAN | 0.83 |
| SQ-29.548 | 0.18 |
| 18 | 0.07 |
| STANDARD DEVIATION <5% | |

[1]IC 50: Means compounds concentrations reducing of 50% of maximum contraction amplitude caused by 5 μg de U-46619.

Test description according to:
Harris N., Greenberg R., Phillips M. B., Michel I. M., Goldenberg H. J., Haslanger M. F., Steinbacher T.E.,— Effects of SQ-27,427, a thromboxane A2 receptor antagonist, in the human platelet and isolated smooth muscle.—*Eur. J. Pharmacol.*, 1984, 103, 9–18.

TABLE 1

| COMPOUND NUMBER | SYNTHESIS METHOD | X | Y$_1$ | Y$_2$ | Z | R$_1$ | R$_2$ | PF, °C. | YIELDING, (%) |
|---|---|---|---|---|---|---|---|---|---|
| 1 | 1.3. | NO$_2$ | NH | NH | O | cycloheptyl | isopropyl | 153–155 | 74,6 |
| 2 | 1.3. | NO$_2$ | NH | NH | O | cyclopentyl | isopropyl | 141–143 | 72,3 |
| 3 | 1.5.2. | NO$_2$ | NH | NH | N—CN | m-toluyl | isopropyl | 170–172 | 62,0 |
| 4 | 1.5.2. | NO$_2$ | NH | NH | N—CN | cyclopentyl | cyclohexyl | 172–174 | 51,5 |
| 5 | 1.5.2. | NO$_2$ | NH | NH | N—CN | cyclohexyl | cyclohexyl | 179–181 | 58,7 |
| 6 | 1.5.2. | NO$_2$ | NH | NH | N—CN | m-toluyl | cyclohexyl | 175–177 | 33,7 |
| 7 | 1.5.2. | NO$_2$ | NH | NH | N—CN | cyclohexyl | isopropyl | 168–170 | 32,2 |
| 8 | 1.5.2. | NO$_2$ | NH | NH | N—CN | cycloheptyl | isopropyl | 153–155 | 46,0 |
| 9 | 1.5.2. | NO$_2$ | NH | NH | N—CN | cyclooctyl | isopropyl | 148–150 | 36,2 |
| 10 | 1.6.2. | NO$_2$ | NH | NH | CH—NO$_2$ | m-toluyl | cyclohexyl | 176–178 | 46,5 |
| 11 | 1.4. | NO$_2$ | NH | NH | S | m-toluyl | isopropyl | 134–136 | 60,8 |
| 12 | 1.4. | NO$_2$ | NH | NH | S | cycloheptyl | isopropyl | 146–148 | 66,5 |
| 13 | 1.3. | NO$_2$ | NH | NH | O | cyclohexyl | isopropyl | 149–151 | 70,1 |
| 14 | 1.4. | NO$_2$ | NH | NH | S | cyclohexyl | isopropyl | 140–142 | 34,4 |
| 15 | 1.4. | NO$_2$ | NH | NH | S | cyclooctyl | isopropyl | 160–162 | 52,5 |
| 16 | 1.4. | NO$_2$ | NH | NH | S | cyclohexyl | cyclohexyl | 167–169 | 40,8 |
| 17 | 1.3. | NO$_2$ | NH | NH | O | cyclohexyl | cyclohexyl | 181–183 | 50,2 |
| 18 | 1.5.2. | NO$_2$ | NH | — | N—CN | m-toluyl | [homopiperidine] | 161–163 | 5,4 |
| 19 | 1.3. | NO$_2$ | NH | NH | O | m-toluyl | tert-butyl | 81–83 | 75,2 |
| 20 | 1.3. | NO$_2$ | NH | NH | O | propyl | isopropyl | 138–140 | 80,8 |
| 21 | 1.3. | NO$_2$ | NH | NH | O | benzyl | isopropyl | 144–146 | 74,3 |
| 22 | 1.3. | NO$_2$ | NH | NH | O | cycloheptyl | cyclohexyl | 174–176 | 48,8 |
| 23 | 1.3. | NO$_2$ | NH | NH | O | cyclooctyl | cyclohexyl | 150–152 | 45,4 |
| 24 | 2.4. | CN | NH | NH | O | m-toluyl | isopropyl | 133–135 | 28,3 |
| 25 | 1.3. | NO$_2$ | NH | NH | O | cycloheptyl | tert-butyl | 135–137 | 68,2 |
| 26 | 1.3. | NO$_2$ | NH | NH | O | cyclooctyl | tert-butyl | 136–138 | 61,3 |
| 27 | 1.3. | NO$_2$ | NH | NH | O | cyclohexyl | ethyl | 163–164 | 72,2 |
| 28 | 1.3. | NO$_2$ | NH | NH | O | cycloheptyl | ethyl | 153–155 | 74,3 |
| 29 | 1.3. | NO$_2$ | NH | NH | O | cyclohexyl | tert-butyl | 147–149 | 70,2 |
| 30 | 1.3. | NO$_2$ | NH | NH | O | o-toluyl | isopropyl | 109–111 | 74,3 |
| 31 | 1.3. | NO$_2$ | NH | NH | O | phenyl | allyl | 150–152 | 53,2 |
| 32 | 1.3. | NO$_2$ | NH | NH | O | cyclohexyl | allyl | 152–154 | 56,3 |
| 33 | 1.3. | NO$_2$ | NH | NH | O | cycloheptyl | allyl | 138–140 | 58,2 |
| 34 | 1.3. | NO$_2$ | NH | NH | O | cyclooctyl | allyl | 159–161 | 47,3 |
| 35 | 1.4. | NO$_2$ | NH | NH | S | propyl | isopropyl | 151–153 | 72,7 |
| 36 | 1.4. | NO$_2$ | NH | NH | S | benzyl | isopropyl | 149–151 | 62,8 |
| 37 | 1.4. | NO$_2$ | NH | NH | S | cyclopentyl | isopropyl | 156–158 | 68,9 |
| 38 | 1.4. | NO$_2$ | NH | NH | S | cyclohexyl | isopropyl | 149–151 | 63,7 |
| 39 | 1.4. | NO$_2$ | NH | NH | S | cycloheptyl | ethyl | 162–164 | 62,4 |
| 40 | 1.4. | NO$_2$ | NH | NH | S | cycloheptyl | cyclohexyl | 172–174 | 38,3 |
| 41 | 1.4. | NO$_2$ | NH | NH | S | cyclooctyl | cyclohexyl | 177–179 | 30,3 |
| 42 | 1.4. | NO$_2$ | NH | NH | S | cyclohexyl | furfuryl | 168–169 | 27,2 |
| 43 | 2.4. | CN | NH | NH | O | cyclohexyl | isopropyl | 148–150 | 32,3 |
| 44 | 1.3. | NO$_2$ | NH | NH | O | cyclooctyl | ethyl | 154–155 | 60,8 |
| 45 | 1.7. | NO$_2$ | NH | NH | O | cyclopentyl | ethyl | 147–149 | 27,4 |
| 46 | 1.3. | NO$_2$ | NH | NH | O | caproyl | isopropyl | 132–134 | 25,8 |
| 47 | 1.3. | NO$_2$ | NH | NH | O | adamantyl | tert-butyl | 169–171 | 54,3 |
| 48 | 1.3. | NO$_2$ | NH | NH | O | cyclododecyl | isopropyl | 162–164 | 50,8 |

TABLE 1-continued

| COMPOUND NUMBER | SYNTHESIS METHOD | X | $Y_1$ | $Y_2$ | Z | $R_1$ | $R_2$ | PF, °C. | YIELDING, (%) |
|---|---|---|---|---|---|---|---|---|---|
| 49 | 1.3. | $NO_2$ | NH | NH | O | 2,3-dimethylphenyl | isopropyl | 146–148 | 28,3 |
| 50 | 1.3. | $NO_2$ | NH | NH | O | p-toluyl | isopropyl | 132–134 | 70,8 |
| 51 | 1.5.2. | $NO_2$ | NH | NH | N—CN | m-toluyl | tert-butyl | 180–182 | 25,3 |
| 52 | 1.3. | $NO_2$ | NH | NH | O | o-toluyl | tert-butyl | 90–92 | 71,4 |
| 53 | 1.3. | $NO_2$ | NH | NH | O | 3-carboxyphenyl | isopropyl | 167–169 | 24,2 |
| 54 | 1.3. | $NO_2$ | NH | NH | O | norbornyl | isopropyl | 177–179 | 48,3 |
| 55 | 1.3. | $NO_2$ | NH | NH | O | norbornyl | tert-butyl | 111–113 | 45,4 |
| 56 | 1.3. | $NO_2$ | NH | NH | O | tert-butyl | isopropyl | 165–167 | 58,3 |
| 57 | 1.3. | $NO_2$ | NH | NH | O | hexyl | isopropyl | 126–128 | 75,4 |
| 58 | 1.3. | $NO_2$ | NH | NH | O | adamantyl | isopropyl | 179–181 | 43,8 |
| 59 | 1.3. | $NO_2$ | NH | NH | O | hexyl | tert-butyl | 112–114 | 72,8 |
| 60 | 1.3. | $NO_2$ | NH | NH | O | decyl | isopropyl | 99–101 | 58,3 |
| 61 | 1.3. | $NO_2$ | NH | NH | O | cyclohexyl | pentyl | 138–140 | 60,2 |
| 62 | 1.3. | $NO_2$ | — | NH | O | [morpholine] | isopropyl | 183–185 | 28,3 |
| 63 | 1.3. | $NO_2$ | — | NH | O | [morpholine] | tert-butyl | 172–174 | 25,4 |
| 64 | 1.3. | $NO_2$ | — | NH | O | [homopiperidine] | isopropyl | 110–112 | 22,1 |
| 65 | 1.3. | $NO_2$ | NH | NH | O | cyclohexyl | phenyl | 178–180 | 27,4 |
| 66 | 2.4. | CN | NH | NH | O | norbornyl | isopropyl | 149–151 | 24,7 |
| 67 | 1.3. | $NO_2$ | NH | NH | O | p-toluyl | tert-butyl | 126–128 | 64,3 |
| 68 | 3.6. | $NO_2$ | NH | NH | O | 2-cyclohexenyl | isopropyl | 156–158 | 23,8 |
| 69 | 3.6. | F | NH | NH | O | 2-cyclohexenyl | isopropyl | 127–129 | 12,8 |
| 70 | 3.6. | CL | NH | NH | O | 2-cyclohexenyl | isopropyl | 132–134 | 15,3 |
| 71 | 3.6. | BR | NH | NH | O | 2-cyclohexenyl | isopropyl | 143–145 | 18,4 |
| 72 | 3.6. | I | NH | NH | O | 2-cyclohexenyl | isopropyl | 148–150 | 17,6 |
| 73 | 1.3. | $NO_2$ | NH | NH | O | 2,3-dimethylphenyl | tert-butyl | 159–161 | 24,8 |
| 74 | 1.5.2. | $NO_2$ | NH | NH | N—CN | cyclohexyl | tert-butyl | 192–194 | 35,8 |
| 75 | 1.3. | $NO_2$ | NH | NH | O | 1-phenylthyl (rac.) | isopropyl | 108–110 | 38,4 |
| 76 | 1.3. | $NO_2$ | NH | NH | O | 1-phenylthyl (rac.) | tert-butyl | 146–148 | 35,2 |
| 77 | 1.3. | $NO_2$ | NH | NH | O | 1-phenylthyl (S) | isopropyl | 108–110 | 28,3 |
| 78 | 1.3. | $NO_2$ | NH | NH | O | 1-phenylthyl (S) | tert-butyl | 113–115 | 25,4 |
| 79 | 1.3. | $NO_2$ | NH | NH | O | 1-phenylthyl (R) | isopropyl | 108–110 | 23,1 |
| 80 | 1.3. | $NO_2$ | NH | NH | O | 1-phenylthyl (R) | tert-butyl | 113–115 | 22,8 |
| 81 | 1.3. | $NO_2$ | NH | NH | O | cyclohexyl | propyl | 137–139 | 78,8 |
| 82 | 1.3. | $NO_2$ | NH | NH | O | cyclohexyl | butyl | 158–160 | 72,1 |
| 83 | 1.3. | $NO_2$ | NH | NH | O | cyclohexyl | hexyl | 115–117 | 70,8 |
| 84 | 1.3. | $NO_2$ | NH | NH | O | cyclohexyl | heptyl | 117–119 | 76,3 |
| 85 | 1.3. | $NO_2$ | NH | NH | O | cyclohexyl | octyl | 93–95 | 65,4 |
| 86 | 1.3. | $NO_2$ | NH | NH | O | 2,4,6-trimethylphenyl | isopropyl | 170–172 | 20,8 |
| 87 | 1.3. | $NO_2$ | NH | NH | O | 3,4-dimethylphenyl | isopropyl | 149–151 | 35,4 |
| 88 | 1.3. | $NO_2$ | NH | NH | O | 3,5-dimethylphenyl | isopropyl | 147–149 | 18,8 |
| 89 | 1.3. | $NO_2$ | NH | NH | O | 2,5-dimethylphenyl | isopropyl | 148–150 | 27,3 |
| 90 | 1.3. | $NO_2$ | NH | NH | O | 2,4-dimethylphenyl | isopropyl | 162–164 | 35,4 |
| 91 | 1.3. | $NO_2$ | NH | NH | O | 2,6-dimethylphenyl | isopropyl | 148–150 | 20,2 |
| 92 | 1.3. | $NO_2$ | NH | NH | O | 2,4,6-trimethylphenyl | pentyl | 146–148 | 18,2 |
| 93 | 3.6. | I | NH | NH | O | 2-cyclohexenyl | pentyl | 148–150 | 14,3 |
| 94 | 1.3. | $NO_2$ | NH | NH | O | o-toluyl | pentyl | 127–129 | 68,4 |
| 95 | 1.3. | $NO_2$ | NH | NH | O | p-toluyl | pentyl | 146–148 | 70,1 |
| 96 | 1.3. | $NO_2$ | NH | NH | O | m-toluyl | pentyl | 129–131 | 71,2 |
| 97 | 2.4. | CN | NH | NH | O | cyclohexyl | pentyl | 144–146 | 27,8 |

What is claimed is:

1. Benzene-sulphonamide compounds having the formula (I): (I)

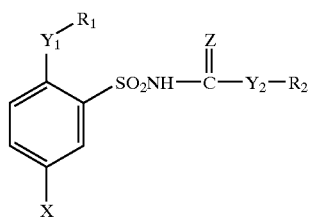

in which:

X represents a nitro, cyano, or halogen group;

$Y_1$ represents a secondary or tertiary amino group, or a sulphur;

$Y_2$ represents a NH group, or a nitrogen atom;

Z represents oxygen, sulphur, =N—CN or =CH—$NO_2$; and $R_1$ and $R_2$, which can be identical or different, represent each independently a saturated or unsaturated linear or branched alkyl group with 2 to 12 carbon atoms, a saturated or unsaturated alicyclic group with 3 to 12 carbon atoms, an aryl group optionally substituted by one or several alkyl groups with 1 to 4 carbon atoms, nitro, cyano, trifluoromethyl, carboxy and halogen groups, or an arylalkyl group or $Y_1$ represents a tertiary amino group and forms with $R_1$ a morpholinyl or homopiperidinyl group, and $Y_2$ represents a nitrogen atom and forms with $R_2$ a homopiperidinyl group with the exception of compounds for which X is a nitro group, $Y_1$ represents a secondary amino group (—NH—), $Y_2$ represents a NH group, Z represents an oxygen, $R_2$ represents an isopropyl and $R_1$ is selected from a group consisting of m-toluyl, phenyl and cyclooctyl, and with the exception of N-[(2- cyclooctylamino-5-cyanobenzene)sulfonyl]N'-isopropyl urea.

2. The compound according to claim 1, characterized in that X is selected from a group consisting of nitro, cyano, bromo and iodo.

3. The compound according to claim 1, characterized in that $Y_1$ represents a NH group and $Y_2$ represents a NH group.

4. The compound according to claim 1, characterized in that $R_1$ and $R_2$ represent each independently an ethyl, butyl, tert-butyl, propyl, isopropyl, pentyl, hexyl, heptyl, octyl, decyl, amyl, cyclopropyl, cyclobutyl, cyclopentyl, cyclohexyl, cycloheptyl, cyclooctyl, cyclododecyl, 2-cyclohexenyl, m-toluyl, o-toluyl, p-toluyl, phenyl, allyl, adamantyl, norbornyl, 3-carboxyphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,6-trimethylphenyl, furfuryl, benzyl or 1-phenylethyl group.

5. The compound according to claim 1, characterized in that it is a salt selected from a group consisting of sodium salts, the potassium salts or organic acid salts.

6. The compound according to claim 5, characterized in that it is chosen in a group having:

N-[(2-cyclohexylamino-5-nitrobenzene)sulfonyl]N'-tert-butyl urea,

N-cyano-N'-[(2-metatoluylamino-5-nitrobenzene)sulfonyl] homopiperidinoamidine,

N-[(2-cycloheptylamino-5-nitrobenzene)sulfonyl]N'-cyclohexyl thiourea, and

N-[(2-cyclohexen-2-yl-5-iodobenzene)sulfonyl]N'-pentyl urea.

* * * * *